United States Patent [19]

Frevel

[11] Patent Number: 4,504,452

[45] Date of Patent: Mar. 12, 1985

[54] COPRODUCTION OF PERCHLOROETHYLENE, PHOSGENE, AND SILICON TETRACHLORIDE

[76] Inventor: Ludo K. Frevel, 1205 West Park Dr., Midland, Mich. 48640

[21] Appl. No.: 532,893

[22] Filed: Sep. 16, 1983

[51] Int. Cl.³ .............................................. C01R 33/08
[52] U.S. Cl. ............................... 423/341; 260/544 K; 570/230
[58] Field of Search ............... 423/341, 342; 570/230; 260/544 K

[56] References Cited

U.S. PATENT DOCUMENTS

| | | | |
|---|---|---|---|
| 1,930,350 | 10/1933 | Strosacker et al. | 570/237 |
| 2,381,001 | 8/1945 | Patnode et al. | 570/217 |
| 3,364,272 | 1/1968 | Ager | 570/217 |

OTHER PUBLICATIONS

Peter P. Budnikoff et al., "Darstellung des Siliciumtetrachlorids", Zeitschrift für angewandte Chemie, vol. 39, p. 765, (1926).
Halogen Chemistry, vol. 2, p. 177-178 and 224, (1967), a multi-volume book edited by Viktor Guttman, Academic Press, London/New York, Subchapter ii: "Silicon Tetrachloride".
Lothar Meyer, "Über die Einwirkung von Chlorkohlenstoff auf Oxyde", Berichte der Deutschen Chemischen Gesellschaft, vol. 20, pp. 681–683, (1887), esp. p. 683, lines 3–7.

Primary Examiner—L. Dewayne Rutledge
Assistant Examiner—Christopher W. Brody
Attorney, Agent, or Firm—William Miller Yates

[57] ABSTRACT

Perchloroethylene, phosgene, and silicon tetrachloride are coproduced by passing vaporous carbon tetrachloride into contact with porous silica at a temperature of 800° to 950° C. The silica is disposed as a bed of granules have a surface area of from 0.1 to 30 m²/g. It should be at least 90 percent pure and free of elemental carbon. Molecular oxygen and water vapor are excluded. The carbon tetrachloride is supplied in a proportion more than two mols per mol of silica consumed.

10 Claims, 2 Drawing Figures

COPRODUCTION OF PERCHLOROETHYLENE, PHOSGENE, AND SILICON TETRACHLORIDE

BACKGROUND OF THE INVENTION

1. Field of the Invention

The invention is a process for coproducing perchloroethylene, phosgene, and silicon tetrachloride by contacting carbon tetrachloride with porous silica at a temperature from 800° to 950° C.

2. Prior Art

Perchloroethylene ($C_2Cl_4$; tetrachloroethylene), phosgene ($COCl_2$; carbonic dichloride), and silicon tetrachloride ($SiCl_4$; tetrachlorosilane) are all widely used in industry. Processes for making them individually are well known but the coproduction of all three seems not to have been carried out heretofore.

Perchloroethylene is usually made by the pyrolysis of carbon tetrachloride ($CCl_4$; tetrachloromethane) at a temperature of 600° to 1500° C. In commercial practice, the pyrolysis is conducted in a furnace by contacting carbon tetrachloride vapor with a heated porous bed of carbon or silicon carbide shapes (U.S. Pat. No. 1,930,350).

Phosgene is commonly produced by the reaction of carbon monoxide and chlorine.

Silicon tetrachloride may be made by the reaction of silica in a heated porous bed with chlorine and carbon (coke) or with phosgene (Halogen Chemistry, vol. 2, p. 177–179 (1967), V. Gutmann ed., Academic Press, London/New York). However, it has been reported that little or no silicon tetrachloride is produced when carbon tetrachloride is passed over silica or silicic acid, even at a red heat (L. Meyer, Ber. 20, 681–683 (1887)).

Perchloroethylene and phosgene have been coproduced from carbon tetrachloride, but carbon monoxide is an essential reactant, the temperature is 150° to 300° C., and an unusual catalyst is required (U.S. Pat. No. 3,364,272).

Perchloroethylene and chlorosilanes have been coproduced from carbon tetrachloride, but only by reacting the latter with elemental silicon in the presence of a metallic catalyst. Temperatures above 300° C. must be avoided to minimize carbonization (U.S. Pat. No. 2,381,001).

Phosgene has apparently never been coproduced with silicon tetrachloride. Rather, in contact with silica at 1000° C., phosgene is consumed, being converted to silicon tetrachloride (Budnikoff, Z. angew, Ch. 39, 765 (1926)).

SUMMARY OF THE INVENTION

In the present invention, perchloroethylene, phosgene, and silicon tetrachloride, all three, are coproduced by a straightforward process which requires no catalyst.

The new procedure comprises contacting carbon tetrachloride with porous silica having a surface area from about 0.1 to about 30 m²/g at a reaction temperature between about 800° and about 950° C. Conveniently, the carbon tetrachloride is passed as a vapor through a bed of the silica in granular form. The reaction product leaves as a stream which is collected, condensed to liquid form, and distilled fractionally or otherwise treated to separate and recover individually the desired perchloroethylene, phosgene, and silicon tetrachloride. Chlorine is also produced and may be recovered.

The chemical reactions occurring in the process may be summarized by the overall equation:

$$2xCCl_4 + SiO_2 \rightarrow (x-1)C_2Cl_4 + 2COCl_2 + SiCl_4 + 2(x-1)Cl_2$$

in which x has a positive value more than one.

As the equation shows, the proportion of carbon tetrachloride should be substantially more than two mols per mol of silica consumed. Preferred operating range is from about 3 to about 10 mols per mol, corresponding to an x value from about 1.5 to about 5.

In practice, the desired products are seldom formed in precisely the stoichiometric proportions indicated by the equation. Competing reactions and the formation of complex byproducts occur to a minor degree. These can be controlled somewhat by regulating process conditions. For best results, water and molecular oxygen should be excluded from the carbon tetrachloride stream. The silica is preferably at least 90 percent pure.

The process is endothermic. High temperature heat must be supplied to provide the energy of reaction and also to offset heat loss from the equipment and thus keep the silica bed at the reaction temperature.

The new process has the advantage that pressure is not required, the reaction zone being at substantially atmospheric pressure. No catalyst is used. Elemental carbon (coke) is not formed.

THE DRAWINGS

The invention may be explained with reference to the drawings which show diagrammatically an arrangement of equipment for carrying out the new process on an industrial scale. In the drawings FIG. 1 illustrates a reactor, silica preheater, and auxiliary apparatus in which reaction according to the invention takes place, forming a product vapor stream, and FIG. 2 illustrates a recovery system in which the product vapor stream is separated into its components.

DETAILED DESCRIPTION OF THE INVENTION

Figure 1:
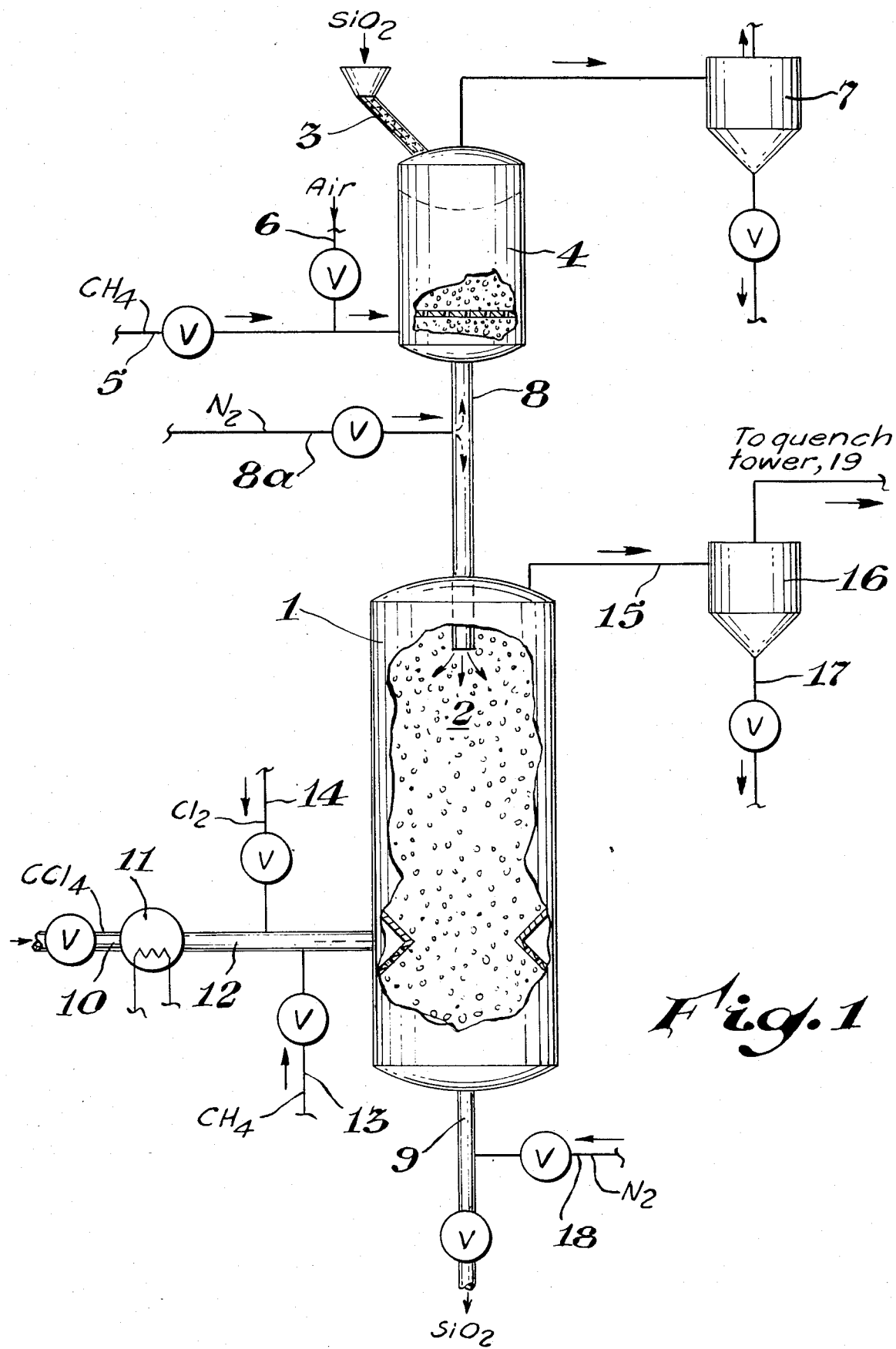
Figure 2:
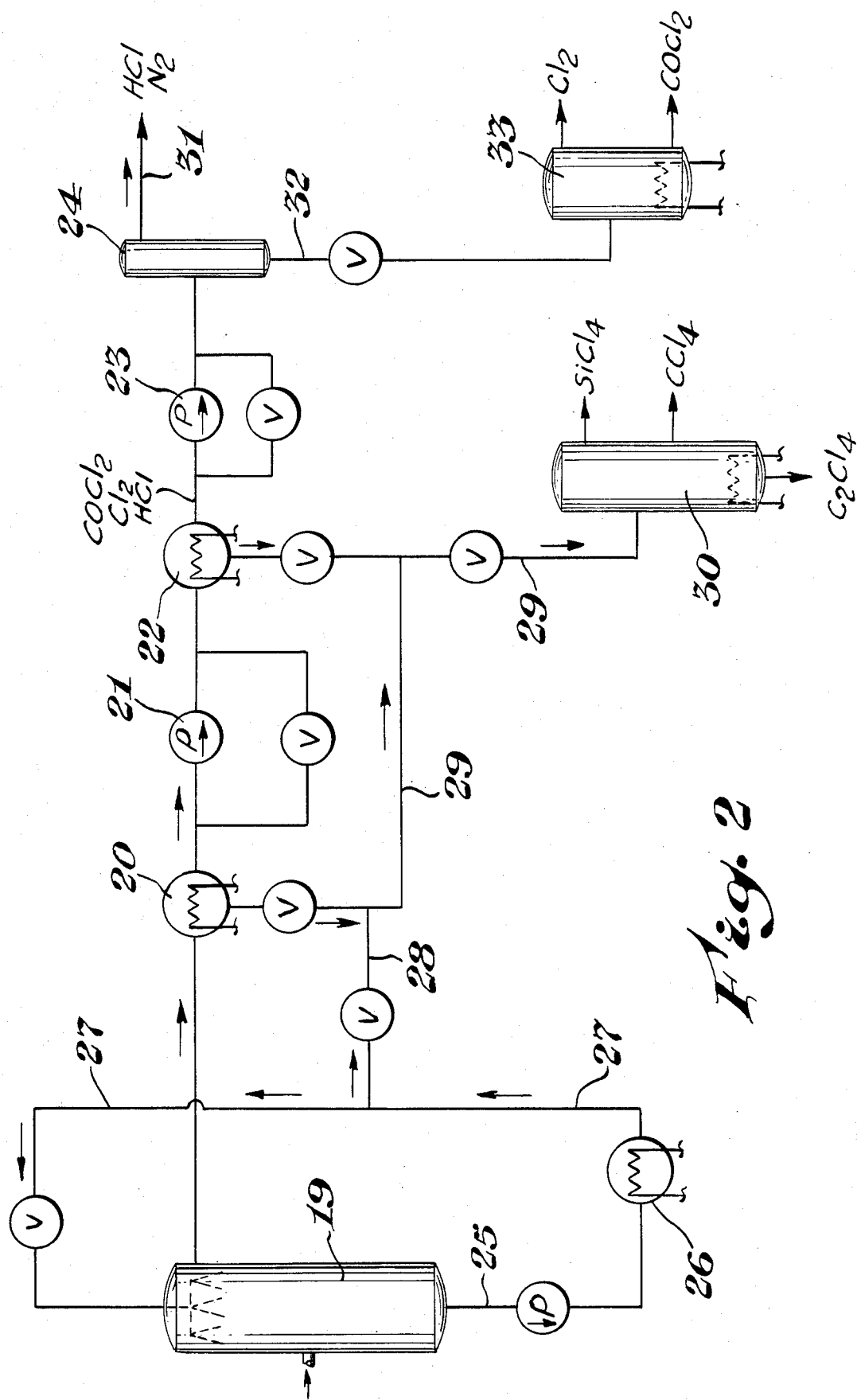

The process of the invention, broadly stated, comprises passing vaporized carbon tetrachloride through a highly heated body of porous silica, collecting the resulting reaction gases, and recovering perchloroethylene, phosgene, and silicon tetrachloride from them.

The temperature in the reaction zone is measured as the peak temperature in the silica bed. It should be from about 800° to about 950° C. Below about 800°, formation of the desired products occurs, if at all, only very slowly. Somewhat above 950°, the carbon tetrachloride tends to pyrolyze to carbon and chlorine. Coke may form, seriously complicating the process by catalyzing formation of unwanted byproducts. At 800° to 950°, reaction proceeds smoothly, and the silica bed remains substantially free of elemental carbon. When cooled, it is usually white in color.

To insure reaction with carbon tetrachloride, the silica should have very high surface area per unit weight, ranging from about 0.1 to about 30 m²/g (square meters per gram) as measured by the B.E.T. method (International Encyclopedia of Chemical Science, D. Van Nostrand Company, Inc., Princeton, N.J., 1964, p. 167). Areas in the higher end of the range, e.g. above 1.0 m²/g are preferred to achieve high reaction rate. Higher surface areas also tend to favor production of phosgene and silicon tetrachloride relative to perchloroethylene.

To avoid handling extremely fine powder, the silica is used in the form of relatively coarse (but highly porous) granules with diameters preferably in the range 5 to 15 mm. The silica may be naturally occurring, such as silica-rich diatomaceous earth (kieselguhr), or synthetic, such as dehydrated silicic acid (e.g. silica gel dehydrated at a temperature of 700° to 900° C.), provided it has the appropriate porosity. To minimize unwanted side reactions, the silica should be at least 90 percent pure (contain 90 percent $SiO_2$ by weight), preferably 95 percent or more, the balance if any being metallic silicates usually found in association with silica. Silica granules of satisfactory purity, porosity, and size are available commercially, e.g. the product Cellite.

The process is best carried out in the substantial absence of water vapor and molecular oxygen. In significant proportion these react with carbon tetrachloride to decrease the yield of intended products and complicate final separation and recovery. The silica, before feeding to the reaction zone, is preferably oven- or kiln-dried to remove occluded moisture. It may also need to be calcined if it contains water chemically bound. Calcining also serves to destroy any carbonaceous matter present. Carbon tetrachloride of commercial grade usually needs no special treatment. To exclude oxygen, normal care is taken to avoid exposure to or entry of air in handling the carbon tetrachloride and silica and in feeding them to the reaction zone. Advantageously the feed channels and the zone itself are kept under slight positive pressure of a dry gas chemically inert to the reactants, such as dry nitrogen. Such gas, when introduced as a stream, also acts as a carrier to help convey gaseous reactants and products through the reactor and recovery systems.

In the laboratory, the process of the invention may be conducted in an elongated tube of inert refractory ceramic or metal. In it, the carbon tetrachloride vapor flows over and through the porous silica granules disposed as a bed. The tube is heated externally in a small furnace. The silica bed and the flowing vapors receive heat by contact with the inside wall of the tube and essentially attain as a peak value the temperature of the wall. Reaction temperature is controlled by regulating the furnace, which may be electric or gas-fired.

On an industrial scale, the reaction may take place in a thermally insulated gas-solid contact reactor vessel or refractory metal lined with non-porous ceramic material, such as refractory brick. In it, the silica is held as a bed, compact or slowly flowing downward. Reaction temperature is maintained by utilizing one or both of the reactants themselves to carry into the reaction zone sufficient heat to maintain the endothermic reaction and to compensate for heat losses from the reactor. To this end, the silica granules may be superheated outside the reaction vessel to a temperature sufficiently higher than the desired reaction temperature to supply the needed heat.

Superheating of the silica may be achieved by any conventional method, as by direct contact with sufficiently hot gases from the combustion of methane or other fuel gas with air. Superheating of the carbon tetrachloride may likewise be by any adequate means which does not subject it to extreme temperature long enough to cause decomposition. Especially suitable is direct mixing with the hot gaseous product of the high-temperature perchlorination of a normally gaseous hydrocarbon, such as methane, with chlorine. This perchlorination product consists mainly of carbon tetrachloride, which becomes added to the stream of carbon tetrachloride feed, and hydrogen chloride, which serves as a carrier gas.

A major controllable variable is the mol ratio of the carbon tetrachloride fed to the silica reacted. As will be appreciated, even with the most porous silica, only a part of each granule is in reactive contact with the carbon tetrachloride at any instant. The remainder, until reached, is in effect an inert support. The mol ratio to be controlled is thus measured relative to the silica reacted, not the total present. Reacted silica may be determined by measurement of the silicon tetrachloride produced.

This ratio, in the invention, should be substantially more than two, and preferably in the range 3 to 10 or more. Most simply, the ratio is controlled by regulating the rate of flow of the carbon tetrachloride vapor through the silica bed. A higher rate of flow reduces the time during which any given unit part of the vapor stream is in contact with the silica. As seen from the overall chemical equation above, higher flow rate, i.e. shorter residence time, results in a higher proportion of perchloroethylene product relative to the phosgene and silicon tetrachloride. At longer times, especially at temperatures around 850° C., the reverse is true. The proportion is not stoichiometrically exact, since in any practical apparatus a part of the carbon tetrachloride unavoidably passes through unreacted. In general, within the preferred ratios of reactants, the residence time of the carbon tetrachloride in a reaction zone of practical configuration will fall in the range 10 to 60 seconds.

In the process, the effluent stream from the reaction zone contains the desired perchloroethylene, phosgene, and silicon tetrachloride products as well as chlorine, unreacted carbon tetrachloride, carrier gas, and usually traces of byproducts. All these may be separated and recovered by conventional techniques. Ordinarily, the effluent stream is cooled to condense perchloroethylene, phosgene, and silicon tetrachloride as a liquid mixture, which may also contain part of any unreacted carbon tetrachloride and of any readily condensable byproducts. This liquid condensate is separated from uncondensed gases and resolved into its components by fractional distillation, the major components being the products desired.

Any unreacted carbon tetrachloride also thus recovered may be recycled to the reaction input. Residual gas uncondensed from the product stream may also be processed to separate and recover its components, especially its chlorine and carrier gas.

The following example illustrates the process of the invention in a preferred mode as carried out on a small laboratory scale.

EXAMPLE

The reactor was a clean fused silica tube ½-inch (12.7 mm) inside diameter and 25 inches (635 mm) long. The porous silica reactant was Cellite granules approximately 1/16-inch (1.5 mm) in diameter, with a surface area (B.E.T.) of about 11 $m^2/g$. A 3.84 gram portion of the granules was loaded into the center of the tube as a small bed held between packing of fused-silica fiber wool. The tube and contents were heated in an electric muffle furnace controlled by a variable transformer to maintain a temperature of 845° C. in the tube. A flow of dry nitrogen (250 ml/min at 25° C. and atmospheric pressure) was first passed through the tube and contents for about an hour to purge air from the entire apparatus, to remove adsorbed moisture and other water, if any, from the granules, and to allow the bed temperature to stabilize. The flow of nitrogen was then switched to pass first through a bubbler and thence into the tube. The bubbler was charged with 23 ml of pure carbon tetrachloride (Baker; I.R. grade) and immersed in a warm water bath regulated at 31° C. Operation was continued for about one hour, during which time 11 ml of the carbon tetrachloride had been vaporized and passed through the silica bed in the reactor. The product gas stream leaving the reactor was fed to a condenser trap cooled in solid carbon dioxide to condense vapors as a mixture of crystals and liquid, about 5 ml.

The liquid condensate in the trap was warmed to thaw the crystals, making it fully liquid, and was analyzed by infra-red absorption techniques and found to contain 17 percent by volume of perchloroethylene, about 5 percent phosgene, and about 6 percent silicon tetrachloride, the balance being unreacted carbon tetrachloride. The gaseous material vented from the trap contained, besides the carrier nitrogen, uncondensed phosgene and carbon tetrachloride, together with some hydrogen chloride and considerable chlorine. The latter, being transparent to infra-red, was not determined. A trace of lemon-yellow crystalline powder was also found deposited near the exit of the reactor but was not identified. The weight loss of the silica due to the reaction was 0.54 g. The silica remaining unreacted in the bed, after cooling, was white, containing no deposit of carbon.

On an industrial scale, the process of the invention may be conducted in apparatus shown schematically in the drawing. While it is not shown, various items of the equipment are made of refractory metal, lined with non-porous ceramic material, and are heavily insulated as needed to withstand the high temperatures in the process and to minimize heat loss.

The reaction of carbon tetrachloride and porous silica takes place in a gas-solid contact vessel or reactor 1 in which granules of porous silica are disposed as a bed 2. The granular silica reactant entering the system is fed by a sloping screw conveyor 3 into a preheater 4. It flows downwardly and is heated by a stream of upwardly flowing hot combustion gases. These are produced from methane entering through an inlet 5 and burning in a combustion zone in a stream of air coming through another inlet 6. The combustion gases, after heating the granules, exhaust to a cyclone separator 7 where any entrained silica is reclaimed for return to the reaction system.

The hot silica granules leave the preheater through a conduit 8 and enter the top of the reactor 1. A small flow of dry nitrogen gas from an inlet 8a is injected into the conduit 8 to maintain a slight positive pressure. A portion of this nitrogen flows downwardly into the reactor, keeping vapors in it from moving upwardly through the conduit. A larger part of the nitrogen flows upwardly into the preheater and assists in purging any residual hot combustion gases in the silica moving downwardly.

Silica granules entering the reaction 1 from the conduit 8 become distributed to form the reaction bed 2. They gradually work downwardly, with the lowermost part being withdrawn continuously through an outlet 9 and recycled to the inlet conveyor 3. A minimal flow of dry nitrogen from a source 18 is fed into the outlet 9 to purge product vapors from the granules being withdrawn.

Carbon tetrachloride reactant in vapor form enters the system through an inlet 10 and flows through a heater 11 and a conduit 12 into the reactor 1. If it is desired to superheat the entering carbon tetrachloride stream, this may be done by mixing it directly with a very hot gas stream produced by admitting methane from the inlet 13 and causing it to undergo perchlorination by burning it in a stream of chlorine from the inlet 14.

In the reactor 1, the hot carbon tetrachloride vapor flows upwardly through the bed of porous silica, forming perchloroethylene, phosgene, and silicon tetrachloride as a product gas mixture. This mixture leaves as a stream through the conduit 15 and goes to the recovery system. It first enters an air-cooled cyclone separator 16. Here entrained silica dust is removed through an outlet 17 to return to the reaction system. Solid by-products, if any, such as ferric chloride (when there is iron oxide impurity in the silica), are also caught in the cyclone 16. If needed, the movement of exiting product vapor to the cyclone may be enhanced by increasing the input of nitrogen from the source 18 to cause it to act as a carrier.

From the cyclone separator 16, the product vapors continue through the recovery system, entering first a quench tower 19, then a heat exchanger 20, a compressor 21, a second heat exchanger 22, a second compressor 23, and a scrubber 24.

In the quench tower 19, the vapor stream is cooled by passing it countercurrent to a shower of relatively cool crude perchloroethylene condensate. The condensate leaves through the bottom outlet 25 and is pumped through a cooler 26 and a line 27 back to the top of the tower 19. Excess liquid condensate may be forwarded from time to time to the liquid recovery system through tie-lines 28 and 29.

The vapor stream leaving the quench is further cooled in the heat exchanger 20, with any condensate formed being sent to recovery through tie-line 29. From the heat exchanger 20, the product vapor goes to a compressor 21 and is cooled again in a second heat exchanger 22 to condense the less volatile portions of the product as a liquid mixture. This mixture goes by the line 29 to a fractionating still 30 in which perchloroethylene product is taken off as bottoms, unreacted carbon tetrachloride as a middle cut, and silicon tetrachloride as overhead.

The more volatile vapors from the heat exchanger 22 go to the second compressor 23 and thence to a scrubber 24. In this, nitrogen carrier gas and any hydrogen chloride survive as gases and leave through outlet 31 for re-use or discard. Condensate from the scrubber 24 goes by way of line 32 to a low-temperature fractionating still 33 in which phosgene is separated from chlorine and both are recovered.

In operating the apparatus of the drawing, the preheater 4 is run to heat the moving silica granules to a temperature above the intended reaction temperature. It should be sufficiently above to supply at least a part of the heat of reaction and to offset heat losses. In general, the silica is superheated to at least 50° above the reaction temperature, as to 900° C. when the reaction is to be at 850°. Recirculation of the silica through preheater and reactor is continuous.

The carbon tetrachloride vapor entering the system by the preheater 11 is usually heated to at least 450° C. When it is desirable to rely on the entering carbon tetrachloride also to supply at least part of the heat needed for reaction, this vapor is further superheated by mixing it with the hot perchlorination product of methane and chlorine from inlets 14 and 13. Here also, superheating at least 50° C. above the reaction temperature is preferred.

The vapors leaving the first compressor 21 are advantageously at about 40° C. and a pressure of 50 pounds gage (4.4 atmospheres). Leaving the second compressor, the temperature may be about 30° C. and the pressure 150 pounds gage (11.2 atmospheres).

The foregoing description is intended to set forth the preferred ways of carrying out the process of the invention. However, it will be understood that numerous modifications and variations may be made within the spirit of the invention and the scope of the following claims.

I claim:

1. A process for the coproduction of perchloroethylene, phosgene, and silicon tetrachloride which comprises contacting carbon tetrachloride with porous silica having a surface area from about 0.1 to about 30 $m^2/g$ at a reaction temperature between about 800° and about 950° C.

2. A process for the coproduction of perchloroethylene, phosgene, and silicon tetrachloride which comprises passing a vapor stream of carbon tetrachloride substantially free of molecular oxygen and water vapor through a bed of porous silica in granular form having a surface area from about 0.1 to about 30 $m^2/g$ and being at least 90 percent pure at a reaction temperature between about 800° and about 950° C., the carbon tetrachloride being supplied in a proportion substantially more than two mols per mol of silica consumed, and separating and recovering perchloroethylene, phosgene, and silicon tetrachloride from the effluent stream of reaction product.

3. A process according to claim 2 in which the surface area of the silica is at least about 1.0 $m^2/g$ and the mol ratio of carbon tetrachloride to silica reacted is from about 3 to about 10.

4. A process according to claim 2 in which the bed of silica is substantially free of elemental carbon.

5. A process according to claim 2 in which unconsumed carbon tetrachloride in the effluent is recycled to the input.

6. A process according to claim 2 in which chlorine is also recovered from the effluent stream.

7. A process according to claim 2 in which a part of the silica is continually withdrawn from the reaction bed, superheated to a temperature sufficiently above the reaction temperature to provide at least part of the heat required to maintain the bed at reaction temperature, and returned to the bed.

8. A process according to claim 2 in which the carbon tetrachloride stream is superheated immediately prior to contact with the silica bed to a temperature sufficiently above the reaction temperature to supply at least part of the heat required to maintain the bed at a reaction temperature by mixing it with a stream of the hot product of the perchlorination of a normally gaseous hydrocarbon with chlorine.

9. A process according to claim 8 in which the hydrocarbon is methane.

10. A process for the coproduction of perchloroethylene, phosgene, and silicon tetrachloride which comprises contacting carbon tetrachloride with porous silica having a surface area from about 0.1 to about 30 $m^2/g$ at a reaction temperature between about 800° and about 950° C., in which the silica is at least 90 percent pure and the carbon tetrachloride is supplied in a proportion substantially more than two mols per mol of silica consumed.

* * * * *